＝ 
US009249345B2

(12) United States Patent
Schweitzer et al.

(10) Patent No.: US 9,249,345 B2
(45) Date of Patent: Feb. 2, 2016

(54) CONCENTRATE FOR MEDICAL SOLUTIONS, PRODUCTION THEREOF AND USE THEREOF IN DIALYSIS

(75) Inventors: Thomas Schweitzer, Schiffsweiler (DE); Thomas Fichert, Sankt Wendel (DE); Pascal Mathis, Bous (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 195 days.

(21) Appl. No.: 13/814,900

(22) PCT Filed: Aug. 17, 2011

(86) PCT No.: PCT/EP2011/064180
§ 371 (c)(1),
(2), (4) Date: Feb. 7, 2013

(87) PCT Pub. No.: WO2012/022775
PCT Pub. Date: Feb. 23, 2012

(65) Prior Publication Data
US 2013/0134357 A1    May 30, 2013

(30) Foreign Application Priority Data
Aug. 18, 2010  (DE) .................... 10 2010 039 489

(51) Int. Cl.
| C09K 3/00 | (2006.01) |
| A61K 9/00 | (2006.01) |
| A61K 9/08 | (2006.01) |
| A61K 9/20 | (2006.01) |
| A61K 33/10 | (2006.01) |
| A61K 33/14 | (2006.01) |

(52) U.S. Cl.
CPC ................ *C09K 3/00* (2013.01); *A61K 9/0019* (2013.01); *A61K 9/08* (2013.01); *A61K 9/2095* (2013.01); *A61K 33/10* (2013.01); *A61K 33/14* (2013.01)

(58) Field of Classification Search
CPC ....................................................... C09K 3/00
USPC ....................................................... 252/364
See application file for complete search history.

(56) References Cited

U.S. PATENT DOCUMENTS

| 2,683,664 | A   |   | 7/1954  | Greer            |         |
|-----------|-----|---|---------|------------------|---------|
| 3,560,380 | A   | * | 2/1971  | Stade            | 252/1   |
| 4,396,382 | A   | * | 8/1983  | Goldhaber        | 604/28  |
| 4,489,535 | A   | * | 12/1984 | Veltman          | 53/431  |
| 4,756,838 | A   | * | 7/1988  | Veltman          | 424/490 |
| 5,108,767 | A   | * | 4/1992  | Mulchandani et al. | 426/72 |
| 6,048,553 | A   | * | 4/2000  | Beckett          | 424/686 |
| 6,117,100 | A   | * | 9/2000  | Powers et al.    | 604/6.11 |
| 6,407,070 | B1  | * | 6/2002  | Kai et al.       | 514/23  |
| 6,475,529 | B2  | * | 11/2002 | Duponchelle et al. | 424/717 |
| 6,489,301 | B1  | * | 12/2002 | Kobira et al.    | 514/23  |
| 6,605,214 | B1  | * | 8/2003  | Taylor           | 210/232 |
| 7,785,611 | B2  | * | 8/2010  | Soni et al.      | 424/278.1 |
| 2002/0012707 | A1 | * | 1/2002  | Duponchelle et al. | 424/717 |
| 2002/0061338 | A1 | * | 5/2002  | Kai et al.       | 424/639 |
| 2005/0031509 | A1 | * | 2/2005  | D'Ayot et al.    | 422/261 |
| 2005/0276868 | A1 | * | 12/2005 | Degreve et al.   | 424/717 |
| 2007/0003637 | A1 |   | 1/2007  | Elisabettini et al. | |
| 2008/0017543 | A1 | * | 1/2008  | Pahlberg et al.  | 206/532 |
| 2012/0323209 | A1 |   | 12/2012 | Falkvall et al.  |         |

FOREIGN PATENT DOCUMENTS

| CN | 1634614        | 7/2005  |
| CN | 101366710      | 2/2009  |
| CN | 101495163      | 7/2009  |
| DE | 247 841        | 7/1987  |
| DE | 247 842        | 7/1987  |
| DE | 247 844        | 7/1987  |
| DE | 20 2005 000 948 | 5/2005 |
| EP | 0 429 679      | 6/1991  |
| EP | 1 059 083      | 12/2000 |
| EP | 1 086 700      | 3/2001  |
| EP | 1 192 960      | 4/2002  |
| EP | 1 192 961      | 4/2002  |
| EP | 1 192 960      | 11/2003 |
| EP | 1 458 433      | 9/2004  |
| JP | H03-128325     | 5/1991  |
| JP | 7299134        | 11/1995 |
| JP | H08-164198     | 6/1996  |
| JP | 2001340423     | 11/2001 |
| JP | 2001-340448    | 12/2001 |
| JP | 2002-080048    | 3/2002  |
| JP | 3589489        | 8/2004  |

(Continued)

OTHER PUBLICATIONS

English Translation of First Office Action dated May 9, 2014 from Chinese Patent Application No. 201180039534.X, pp. 1-8.

(Continued)

*Primary Examiner* — Nicole M Buie-Hatcher
*Assistant Examiner* — M. Reza Asdjodi
(74) *Attorney, Agent, or Firm* — MH2 Technology Law Group, LLP

(57) ABSTRACT

The present invention relates to a novel dry concentrate for producing medical solutions, more particularly dialysis solutions, which comprises electrolyte components, buffer components and an osmotic agent, wherein the concentrate comprises magnesium carbonate instead of magnesium chloride. The use of magnesium carbonate as an electrolyte prevents the formation of slurries. By providing anhydrous glucose as an osmotic agent, and by optionally spatially separating this osmotic agent from other components, the occurrence of caking of the concentrate is additionally avoided. The occurrence of caking is further reduced by providing the buffer component sodium bicarbonate together with sodium chloride separate from all other components. The concentrate of the present invention is particularly suitable for use in multi-chamber container bag systems. The concentrate of the present invention exhibits good dissolution behavior and improved storage stability.

26 Claims, 3 Drawing Sheets

(56) References Cited

FOREIGN PATENT DOCUMENTS

| | | | |
|---|---|---|---|
| JP | 2005-514174 | 5/2005 | |
| JP | 2008239587 | 10/2008 | |
| JP | 11 103 771 | 2/2011 | |
| WO | 97/25959 | 7/1997 | |
| WO | 99/27885 | 6/1999 | |
| WO | WO 9927885 A1 * | 6/1999 | ............... A61J 1/00 |
| WO | 2007/144427 | 12/2007 | |
| WO | 2010/111184 | 9/2010 | |
| WO | 2011/073274 | 6/2011 | |

OTHER PUBLICATIONS

English Translation of Search Report dated Apr. 30, 2014 from Chinese Patent Application No. 201180039534.X, pp. 1-3.

English Translation of Office Action dated Feb. 21, 2014 from European Patent Application No. 11 752 152.6, pp. 1-6.

Anonymous. English Translation of Energy Body Systems. 2009, 5 Pages. XP-002660577 (previously submitted on Feb. 7, 2013).

English Translation of International Preliminary Report on Patentability from International Application No. PCT/EP2011/064180 dated Feb. 28, 2013, 12 Pages.

Anonymous. Energy Body Systems. 2009, 11 Pages. XP-002660577.

Notification of Reasons for Rejection with English Translation dated Mar. 3, 2015 issued in Japanese Patent Application No. 2013-524451, pp. 1-7.

Office Action with English Translation dated Jan. 22, 2015 issued in Chinese Patent Application No. 201180039534, pp. 1-9.

* cited by examiner

CONCENTRATE FOR MEDICAL SOLUTIONS, PRODUCTION THEREOF AND USE THEREOF IN DIALYSIS

CROSS-REFERENCE TO RELATED APPLICATIONS

This application is a U.S. National Stage application of PCT/EP2011/064180 filed 17 Aug. 2011, which claims priority to German patent application 10 2010 039 489.0 filed 18 Aug. 2010, the entire disclosure of which is hereby incorporated herein by reference in its entireties.

The present invention relates to improved concentrates for medical solutions, the production thereof as well as the use thereof in dialysis.

BACKGROUND

Dialysis solutions are typically produced in central facilities of treatment centers and transferred via a tubing system to the individual treatment stations. Alternatively, treatment centers make use of large-volume canisters from which the prepared dialysis solution is conducted to the treatment stations. Such central supply installations for dialysis solutions are problematic with regard to their maintenance and the disinfection of the entire facility. Although these difficulties can be managed reliably, they cause undesirable expenditure.

A disadvantage of having a central supply of dialysis solution is also the lack of individualization in its production, as the needs of individual patients cannot be met by applying a customized composition of the dialysis solution during treatment.

It is therefore increasingly common to produce dialysis solutions directly at the treatment station from initial concentrates. This has the advantage of being able to produce large volumes of solution ready for use in treatment from a small amount of concentrate with minimal effort and being able to control the composition of the solution on an individual basis. A water source and a reverse osmosis (RO) system at the treatment station or close to the treatment station are the only additional components required.

The use of customary physiologically acceptable acidic components, such as hydrochloric acid or acetic acid necessitates a concentrate in a liquid form. Concentrates in a liquid form can be easily dosed by machine, and so the adjustment of solution compositions on an individual basis can be easily performed. More particularly, the composition can also be varied during dialysis treatments, providing possible therapeutic advantages in individual cases.

A disadvantage of the known solution concentrates is that both the production of the liquid form in manufacturing facilities and its transportation necessitates the expenditure of resources which would not be required in the case of solid initial concentrates. First, the container systems usually used for liquid concentrates have to exhibit certain properties. For example, they have to exhibit an appropriate resistance to being dropped, they have to ensure storage stability of the concentrates, and the container material needs to exhibit an appropriate buckling stability. Secondly, liquid concentrates, which are, for example, 125-fold concentrated, comprise a high concentration of acid, leading to a high acidity with pH values in the range from pH 0 to pH 1. Such a concentrate must be considered as hazardous material, which has to be handled professionally and with particular care in the case of accidents, leakages, etc.

Attempts have been made to avoid liquid concentrates and to provide the concentrate in a solid form. However, individualization of the final dialysis solution is then only achieved with considerable effort. Various dry initial concentrates of different compositions can be produced that may be adapted for individual use. For example, variation of the potassium constituents is desired in order to provide dialysis solutions of different potassium concentrations which are customized to fulfil different patient needs.

Dry concentrates are of particular interest for producing a dialysis batch. Here, the entire volume of dialysis solution is produced in one dissolving process and provided for dialysis.

The typical components for the production of a dialysis solution are magnesium chloride, calcium chloride, sodium chloride, potassium chloride, sodium bicarbonate, glucose and a physiologically acceptable acid such as hydrochloric acid, acetic acid or citric acid. In the case of a solid formulation, only solid acids are conceivable as acidic components. In general, liquid acids may partially dissolve the concentrate, which results in a different dosage form, i.e., in a slurry (a suspension with a high solid content).

The combination of the components can lead to physical/chemical incompatibilities, resulting in possible deterioration of the dissolution behaviour of the concentrate and impairing the storage stability.

For example, it is known from the prior art that glucose, which is typically used as an osmotic agent, is not stable when stored together with other components of the concentrate such as citric acid or sodium bicarbonate. However, glucose has a high osmolarity at relatively low concentrations and is well tolerated. A particular advantage of the use of glucose is its relatively low price as compared to other excipients that could be potentially used as osmotic agents.

Various suggestions are known in the prior art to avoid the interaction between glucose and other components in dry concentrates.

EP 1 192 960 B1, EP 1 192 961 B1, JP 200823958, EP 1 086 700 B1 and EP 1 059 083 B1 describe dry concentrates in which granules are formed as multiple layers of the components required for dialysis solution production. Glucose layers, or areas of glucose within a layer, are separated from the other components by separating layers in order to avoid a chemical interaction and/or a degradation of the glucose. The separating layer consists of, for example, sodium chloride.

However, a disadvantage of such granules is that glucose is in contact with sodium chloride, which can lead to caking after prolonged storage. Caking is the process of agglomerate formation of a primarily powdery substance, of granules or of a substance in the form of pellets or tablets. Caking occurs as particles bind and stick together during processes of partial dissolution or other diffusion phenomena. Caking is promoted by the influence of water and heat.

Furthermore, the required electrolyte components magnesium chloride and calcium chloride are hygroscopic and have a tendency to partially form slurries with their hydration water. Slurries comprise solid and dissolved excipients side by side in a liquid phase. The solid content of such a mixture is so high that the appearance is predominated by a pulpy or pasty viscosity.

For the stable storage of dry concentrates, JP 3589489 B2 and EP 1 458 433 A1 suggest to provide the components required for the dialysis solution in multiple layers within one container, wherein glucose is provided with a separating layer of sodium chloride separate from a further, possibly interactive layer, e.g. sodium bicarbonate. The problem of slurry formation caused by the hygroscopy of the components magnesium chloride and calcium chloride is, however, not addressed, and also the problem of caking of glucose and sodium chloride remains unresolved.

JP 2001340423 A2 suggests storing glucose separate from other components in order to avoid the caking of glucose or to avoid degradation of glucose through interaction with other components. However, the problem of slurry formation caused by the electrolyte components magnesium chloride and calcium chloride persists.

SUMMARY

One aspect of the present invention is to provide a concentrate which is storage stable and avoids one or more of the problems mentioned above.

This aspect of the invention is characterized by the features of claim 1. Particular embodiments of this aspect of the invention are characterized in the dependent claims 2-19.

Figure 1:
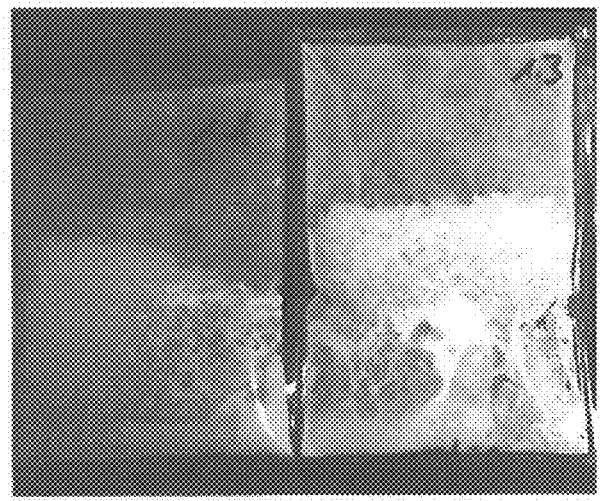
FIG. 1 is a photograph showing, on the left, a container comprised of film material without appreciable gas-barrier properties, and, on the right, a container comprised of film material with a gas-barrier layer of silicon oxide, as discussed in Example 3.

A "concentrate" according to the invention is a component soluble in an aqueous medium, preferably a composition of components which is suitable for use as a medical solution, preferably as a dialysis solution upon the addition of an aqueous medium. The concentrate is preferably provided in a dry form, i.e. as a dry concentrate. Concentrates can also be used in a liquid, semi-solid or pasty form, provided that the stability of the concentrate, the dilution in the dissolving process, interactions with the concentrate container and quality control are not negatively affected. With regard to dosing and application of dry concentrates for the production of concentrate containers, such as, for example, a multi-chamber container system, free-flowing concentrates are preferred. A uniform water content for such dry concentrates cannot be specified, since the content depends on the exact composition of the components of the concentrate. However, the water content should not be so high that caking occurs before or during production or storage of the concentrate container. In a preferred embodiment, a plastic container is used as a concentrate container, whereby free-flowing dry concentrates are preferred for the production process and also for the storage of the concentrate container.

A typical concentrate comprises multiple components, e.g. 2, 3, 4, 5, 6, 7, 8, 9, 10, 12 and up to 20 components, but usually 7, 8 or 9 components. The term "concentrate" does not necessarily refer to the entirety of all components present in the final, ready-to-use medical solution. Rather, further components can be added to the concentrate which, together with the concentrate and water, yield the ready-to-use medical solution. Preferably, the concentrate comprises at least one component selected from the group consisting of a buffer component, an electrolyte component and an osmotic component. In a particularly preferred embodiment, the concentrate comprises at least one buffer component, at least one electrolyte component and at least one osmotic component.

The components comprised in the concentrate can be all typical components of a dialysis solution, e.g., buffer components, such as sodium bicarbonate, lactate, pyruvate, acetate, citrate, TRIS (tris(hydroxymethyl)aminomethane), amino acids or peptides or other buffer components familiar to a person skilled in the art; osmotic components, such as glucose, glucose polymers, such as maltodextrin or icodextrin, cyclodextrin, modified starch, polyols, fructose, amino acids, peptides, proteins, amino sugars, glycerol, N-acetylglucosamine, etc.; electrolyte components, such as sodium chloride, potassium chloride, calcium chloride or magnesium chloride, etc. Furthermore, physiologically acceptable acids can be comprised, whereby the use of solid citric acid is established and is thus preferred. The advantages of citric acid are based on its ease of availability at the required pharmaceutical purity. Furthermore, citric acid has an anticoagulatory effect, so that coagulation can be prevented at blood contact zones, e.g. within the dialysis filter. Optionally, other components may be comprised. The components preferably match the quality requirements of the pharmacopoeia (e.g. Ph. Eur.). The exact composition and quantitative ratios may vary depending on the specific application.

The aqueous medium for producing the medical solution from the concentrate is typically water, preferably reverse-osmosis (RO) water. However, any other acceptable aqueous medium familiar to a person skilled in the art may also be used, e.g. a distillate, or a partial solution which may yield the final medical solution upon addition to the remaining concentrate components according to the invention. Preferably, the final solution is a dialysis solution.

The concentrate components according to the invention may be provided as one mixture. Preferably, however, the various components are provided separately in individual compartments, e.g., in 2 or more individual compartments, preferably in 3, 4 or more individual compartments. A "compartment" according to the invention is a spatial separation of the components. In a particularly preferred embodiment, such compartments are formed by means of a container separated into multiple chambers (multi-chamber container), whereby the compartments are preferably separated from one another by peel seams (seal bonds between films which can be separated without resulting in a film breakage or a delamination of the mostly multilayered films).

Upon filling the multi-chamber container with water, the peel seams are separated and the compartments release the components which are dissolved by the influxing water. The principle of this dissolution method is already described in WO 2007/144427 A2 and in JP 7299134 A2. For the dissolving process of the concentrate, both in a single storage container and in a multi-chamber container system, it is important that the concentrate components are provided in a dry form that is quickly mixable with water. Any previously formed caking products may prevent the dissolution of the components within an acceptable time frame. In addition, the formation of slurries may result in the elution of constituents of the container film (e.g. PVC, PET, plasticizer, adhesive layer) into the slurry mass and contamination of the concentrate. In addition, after the formation of a slurry, a simple optical inspection of the integrity of a concentrate compartment, e.g., an optical inspection for cracks in the film material caused by edged granules is no longer possible.

When the concentrate components are provided separately in different individual compartments, it is necessary to combine various components with one another. The combination of hygroscopic and non-hygroscopic and also acidic and basic components represents a considerable challenge. Various experiments to combine the individual components initially resulted in the following scheme:

| | |
|---|---|
| Electrolyte compartment "A": | Sodium chloride, potassium chloride, calcium chloride, magnesium chloride, citric acid |
| Glucose compartment "B": | Glucose |
| Bicarbonate compartment "C": | Sodium chloride, sodium bicarbonate |

However, it was found that the above-listed partitioning of the components in powder form or granular form in three or more compartments resulted in further problems, which are solved by the present invention.

Firstly, it was found that the hygroscopicity of the required electrolyte components, magnesium chloride ($MgCl_2 \times 6H_2O$) and calcium chloride ($CaCl_2 \times 2H_2O$), causes considerable water uptake into the electrolyte compartment "A". This effect may be attributed to both the uptake of external water via the primary packaging as well as to the dissolution of the salts by their own crystal water.

Said water uptake is highly problematic, since it causes physicochemical changes in the concentrate with several consequences. First, the dissolution behaviour of the concentrate is altered due to the transition of a solid to a semi-solid aggregate state. Additionally, interactions between the components and the primary packaging may occur. Moist components may cause the elution of constituents of the packaging material into the components. Furthermore, film damage of the primary packaging can occur due to changes of granule sizes, e.g., due to crystal growth. If multi-chamber containers are used, a further problem may arise by the transfer of liquid from electrolyte compartment "A" into other compartments through the packing material, which may then cause physicochemical changes of components in these other compartments. For example, the permeation of moisture into bicarbonate compartment "C" could lead to conversion of sodium bicarbonate into sodium carbonate. The associated release of $CO_2$ can negatively affect the pH of the final solution.

Another problem arises by the change of the optical appearance of the concentrate, as the concentrate components may no longer be provided in a dry and solid state in all compartments due to the changes mentioned above. This causes uncertainty for the user, since a decision on whether the product is defective or not cannot be readily made (e.g. if the components of one of many compartments are semi-solid).

The present invention resolves the problem of water uptake by the hygroscopic components by providing a concentrate in which the component magnesium chloride ($MgCl_2 \times 6H_2O$) is replaced by magnesium carbonate.

In particular, it was surprisingly found that the use of magnesium carbonate instead of magnesium chloride results in reduced hygroscopicity and a higher stability of the concentrate. The formation of a slurry is thereby prevented. This leads to an improved dissolution behaviour and facilitates the dosing of the concentrate. Consequently, the permeation of moisture to other components of the concentrate, also to those present in other compartments, is prevented. Consequently, these components remain chemically and physically unaltered, as none of the chemical reactions mentioned above can occur. The migration of constituents of the primary packaging into the bulk material is likewise prevented. In a preferred embodiment, alkaline magnesium carbonate ($4MgCO_3 \times Mg(OH)_2 \times 5H_2O$) is used.

In a further aspect of the invention, a concentrate is provided in which, in addition to the replacement of magnesium chloride ($MgCl_2 \times 6H_2O$) by magnesium carbonate, calcium chloride ($CaCl_2 \times 2H_2O$) is replaced. Instead of calcium chloride of the formula $CaCl_2 \times 2H_2O$, (which is typically used), anhydrous calcium chloride ($CaCl_2$) is used according to the present invention. The application of anhydrous calcium chloride prevents its dissolution in its own hydration water above temperatures of about 30° C. Water uptake into the dry concentrate is most effectively prevented by the combination of alkaline magnesium carbonate and anhydrous calcium chloride.

In a particularly preferred embodiment of the invention, the concentrate according to the invention is provided in a multi-chamber container system. When the concentrate according to the invention is used in such a multi-chamber container, the components magnesium carbonate, preferably alkaline magnesium carbonate, and calcium chloride, preferably in its anhydrous form, are provided together in an electrolyte compartment "A" which is substantially free of magnesium chloride, i.e., the amount of $MgCl_2$ should be lower than 5%, preferably lower than 4%, 3%, 2%, 1%, 0.5%, or 0.1% in percent by weight of the magnesium salts used.

The electrolyte compartment "A" comprises, in addition to the two components magnesium carbonate and calcium chloride, preferably one or more physiologically acceptable acids, such as, for example, citric acid and/or other solid physiologically acceptable acids known in the art, such as, for example, malic acid, fumaric acid, isocitric acid, succinic acid or oxalic acid. In addition, potassium chloride may be present.

Another problem arises from caking of the components. Caking of the components may cause dissolution delays, inhomogeneity or particle formation of the components. In the case of container (bag) systems, caking can also cause film damage which can result in leakage of the entire system.

It has now been found that caking of the components may be reduced and even prevented by applying glucose in the form of anhydrous glucose or by providing glucose spatially separated from the other components, e.g., in a compartment "B". In a preferred embodiment, glucose is provided spatially separated from the other components, in a compartment "B" for example, and in the form of anhydrous glucose.

In a further aspect of the invention, the two components sodium chloride and sodium bicarbonate are provided separately from all the other components, for example, in a bicarbonate compartment "C" which comprises only these two salts and no further components. As a result, caking in this compartment may be prevented, and the dissolution behaviour and the storage stability of the concentrate is further improved.

An exemplary concentrate according to the invention is shown schematically in the following table:

| | |
|---|---|
| Electrolyte compartment "A": | Magnesium carbonate; calcium chloride (preferably anhydrous), potassium chloride, physiologically compatible acid, e.g. citric acid |
| Glucose compartment "B": | Glucose (preferably anhydrous) |
| Bicarbonate compartment "C": | Sodium chloride, sodium bicarbonate |

The individual components of the concentrate according to the invention may be provided in the amounts as listed below. The individual compositions may vary depending on the specific form of the extracorporeal blood treatment or on the type and specific use of the medical solution. The compositions of the concentrates can be adapted in different ways to obtain working solutions which lie in the following composition range:

$Ca^{2+}$: 0-2 mmol/l, e.g. 1.0; 0.8; 1.2; 1.5; 1.7; 0.5; 0.1 or 0.3-1.7; 0.5-1.5; 0.8-1.3 mmol/l $K^+$: 0-130 mmol/l, e.g. 1; 2; 3; 4; 1.5; 2.5; 3.5; 4.5 or 0-5; 1-4; 1.5-3.5; 2-3 mmol/l $HCO_3^-$: 5-40 mmol/l, e.g. 22; 24; 25; 26; 27; 28; 29; 30; 31; 32; 33; 34; 35; 36; 37; 38; 39 or 22-38; 24-36; 25-33; 28-34; 30-37 mmol/l $Na^+$: 10-150 mmol/l, e.g. 113; 118; 123; 125; 125.5; 126; 128; 130; 132; 134; 138; 140; 145; 148; 115-130; 120-128; 124-128; 120-135; 125-135; 130-140 mmol/l $Mg^{2+}$: 0-5 mmol/l; 0.1; 0.3; 0.6; 0.8 or 0.1-0.8; 0.3-0.7; 0.5-0.75 mmol/l Cr: 10-60 mmol/l, 100-140 mmol/l Citric acid: 0-5 mmol/l, e.g. 1; 2; 3; 4; 5 or 0.8-1.5; 0.3-2; 0.4-4; 0.8-3; 1-2.5 mmol/l Glucose: 0-250 mmol/l, e.g. 5.55; 83 mmol/l or 0-10; 60-100 mmol/l pH: pH=6.8-7.8; preferably pH=7-7.6; most preferably pH=7.3 or pH=7.4.

The physiologically acceptable acid is typically present in an excess of 0.5 mmol (based on the original weight of magnesium carbonate). The exact amounts of the components of the concentrate may be selected by a person skilled in the art on the basis of his/her general knowledge and in consideration of the respective patient data or the respective intended purpose in order to obtain the desired medical solutions.

The use of alkaline magnesium carbonate ($4MgCO_3 \times Mg(OH)_2 \times 4H_2O$) in a concentrate according to the invention for producing a medical solution requires a certain dissolution procedure, since alkaline magnesium carbonate is only readily soluble in an acidic medium. A sufficient solubility in the dissolution process is given, e.g., at a pH of ≤4, such as, for example, pH=3. Generally, the dissolution process should not be performed above a pH of 4 in order to avoid any remaining undissolved particles. In one embodiment of the present invention, the dry alkaline magnesium carbonate is provided together with a physiologically acceptable solid acid. The influx of water, or an aqueous medium which is suitable for producing the medical solution, results in a sufficiently acidic pH, so that the alkaline magnesium carbonate is dissolved according to the following reaction scheme and an "acidic base solution" is formed:

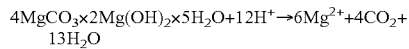

When the production of a dialysis solution or a blood substitute solution is performed with the help of a multichamber container system, the glucose is added, preferably in a subsequent step, from glucose compartment "B", either in a dissolved or partially dissolved form or directly as a dry concentrate, to the above acidic base solution. Alternatively, the dry components of compartments "A" (electrolyte compartment) and "B" (glucose compartment) may be first combined and then dissolved in an aqueous dilution medium.

In a further step, one or more buffer components, or the concentrate of compartment "C" (bicarbonate compartment), comprising one or more buffer components, are added either partially dissolved or directly to the "acidic base solution" previously formed, i.e. to the acidic solution of magnesium carbonate, or to the acidic mixture of the concentrate of the electrolyte compartment "A" comprising magnesium carbonate and a physiologically acceptable acid and diluent, or to a mixture of the concentrates from compartments "A" and "B" and the diluent, which results in a solution having a pH of >4, preferably a pH in the range from 6 to 8, and most preferably a pH in the range from ≥6.8 to ≤7.8. The components of the "acidic base solution" do not necessarily have to be completely dissolved. Preferably, the alkaline magnesium carbonate is already dissolved when the concentrate from compartment "C" is added. This leads to the development of $CO_2$, because the bicarbonate salt is dissolved in the acidic pH range:

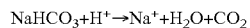

This development of $CO_2$ must be taken into account by means of an appropriate device of the equipment applied for dissolution. Preferably, a ventilation system through which excess $CO_2$ can escape should be used.

The concentrate according to the invention is useful, for example, for producing medical solutions. Medical solutions are preferably dialysis solutions, e.g. a haemodialysis solution or a peritoneal dialysis solution; or blood substitute solutions, e.g., haemofiltration solutions.

The invention will be explained in more detail below by reference to the figures and the examples listed below.

EXAMPLE 1

Exemplary concentrate compositions according to the present invention are as follows:

| | Substance weight [g] | | | | | | |
|---|---|---|---|---|---|---|---|
| | Compartment A | | | | Compartment B | Compartment C | |
| | $MgCO_3$ | $CaCl_2$ | KCl | Citric acid | D-Glucose, anhydrous | Sodium chloride | $NaHCO_3$ |
| Variant 1 | 3.01 | 8.62 | 0 | 11.97 | 62.00 | 391.22 | 166.78 |
| Variant 2 | 3.01 | 8.62 | 9.24 | 11.97 | 62.00 | 391.22 | 166.78 |
| Variant 3 | 3.01 | 8.62 | 18.50 | 11.97 | 62.00 | 391.22 | 166.78 |
| Variant 4 | 4.51 | 0 | 0 | 11.97 | 62.00 | 422.06 | 93.62 |
| Variant 5 | 4.51 | 0 | 9.24 | 11.97 | 62.00 | 422.06 | 93.62 |
| Variant 6 | 4.51 | 0 | 18.50 | 11.97 | 62.00 | 422.06 | 93.62 |

| | Concentrate composition [%] | | | | | | |
|---|---|---|---|---|---|---|---|
| | Compartment A | | | | Compartment B | Compartment C | |
| | $MgCO_3$ | $CaCl_2$ | KCl | Citric acid | D-Glucose, anhydrous | Sodium chloride | $NaHCO3$ |
| Variant 1 | 12.8 | 36.5 | 0.0 | 50.7 | 100.0 | 70.1 | 29.9 |
| Variant 2 | 9.2 | 26.2 | 28.1 | 36.4 | 100.0 | 70.1 | 29.9 |
| Variant 3 | 7.1 | 20.5 | 43.9 | 28.4 | 100.0 | 70.1 | 29.9 |
| Variant 4 | 27.4 | 0.0 | 0.0 | 72.6 | 100.0 | 82.5 | 17.5 |
| Variant 5 | 17.5 | 0.0 | 35.9 | 46.5 | 100.0 | 82.5 | 17.5 |
| Variant 6 | 12.9 | 0.0 | 52.9 | 34.2 | 100.0 | 82.5 | 17.5 |

| | Resulting concentrations [mmol/L] | | | | | | |
|---|---|---|---|---|---|---|---|
| | Compartment A | | | | Compartment B | Compartment C | |
| | $MgCO_3$ | $CaCl_2$ | KCl | Citric acid | D-Glucose, anhydrous | Sodium chloride | $NaHO_3$ |
| Variant 1 | 0.50 | 1.25 | 0.0 | 1.0 | 5.55 | 140.0 | 32.0 |
| Variant 2 | 0.50 | 1.25 | 2.0 | 1.0 | 5.55 | 140.0 | 32.0 |
| Variant 3 | 0.50 | 1.25 | 4.0 | 1.0 | 5.55 | 140.0 | 32.0 |
| Variant 4 | 0.75 | 0.0 | 0.0 | 1.0 | 5.55 | 140.0 | 18.0 |
| Variant 5 | 0.75 | 0.0 | 2.0 | 1.0 | 5.55 | 140.0 | 18.0 |
| Variant 6 | 0.75 | 0.0 | 4.0 | 1.0 | 5.55 | 140.0 | 18.0 |

Composition and concentrations of a typical batch container (bag) before the replacement of $MgCl_2$ by $MgCO_3$ and the use of anhydrous substances (comparative example):

| | Substance weight [g] | | | | | | |
|---|---|---|---|---|---|---|---|
| | Compartment A | | | | Compartment B | Compartment C | |
| | $MgCl_2 \times 6H_2O$ | $CaCl_2 \times H_2O$ | KCl | Citric acid | D-Glucose $\times H_2O$ | Sodium chloride | $NaHCO_3$ |
| Comparative example | 6.32 | 13.64 | 9.24 | 17.36 | 62.00 | 375.1 | 190.34 |

| | Concentrate composition [%] | | | | | | |
|---|---|---|---|---|---|---|---|
| | Compartment A | | | | Compartment B | Compartment C | |
| | $MgCl_2 \times 6H_2O$ | $CaCl_2 \times H_2O$ | KCl | Citric acid | D-Glucose $\times H_2O$ | Sodium chloride | $NaHCO_3$ |
| Comparative example | 13.57 | 29.29 | 19.85 | 37.29 | 100 | 66.34 | 33.66 |

| | Resulting concentrations [mmol/L] | | | | | | |
|---|---|---|---|---|---|---|---|
| | Compartment A | | | | Compartment B | Compartment C | |
| | $MgCl_2 \times 6H_2O$ | $CaCl_2 \times H_2O$ | KCl | Citric acid | D-Glucose $\times H_2O$ | Sodium chloride | $NaHCO_3$ |
| Comparative example | 13.57 | 29.29 | 19.85 | 37.29 | 5.55 | 103.50 | 36.50 |

The concentrates according to the invention are preferably provided in a multi-chamber container system described above. It was found that the above-listed concentrates according to the invention showed no water uptake, no slurrying and no caking. Stability tests of the novel concentrate compositions show a homogeneous solution with excellent stability.

EXAMPLE 2

Figure 2:
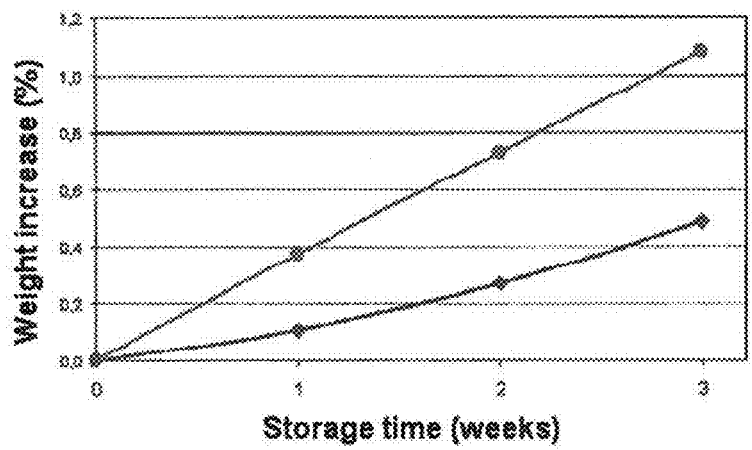
FIG. 2 is a graph illustrating the weight increase over time of concentrate containers having a gas barrier versus gas permeable film material as discussed in Example 2.

The water uptake into electrolyte compartment "A" was evaluated using two different concentrate containers, whereby one is manufactured with a gas-barrier film and the other with a gas-permeable film material. The concentrate consisted of the conventional constituents:
sodium chloride
magnesium chloride with crystal water, $MgCl_2 \times 6H_2O$
calcium chloride with crystal water, $CaCl_2 \times 2H_2O$
potassium chloride, KCl
citric acid, $C_6H_8O_7$ The hermetically sealed containers were stored at 40° C. and 75% relative humidity in a climate chamber and weighed in regular intervals. An increase in the weight of the container can be attributed to permeability to water vapour and the resulting uptake of water into the concentrate. As expected, the gas-permeable film resulted in a faster and also greater weight increase of the concentrate container as compared to the film having a gas barrier (see also FIG. 2, which depicts the weight increase of the concentrate container having a gas-barrier film (♦) or gas-permeable film material (●) respectively, and containing the concentrate comprising sodium chloride, KCl, $CaCl_2$, $MgCl_2$, citric acid at 40° C. and 75% relative humidity.)

The gas-permeable film was manufactured using the following raw materials:
Polypropylene, -PP-
Polyethylene, -PE-
Styrene ethylene butylene styrene block copolymer, -SEBS- The gas-impermeable film additionally contained a ceramic barrier layer made of silicon oxide.

The water uptake into a concentrate container (bag) with a gas-barrier film or with a gas-permeable film material was also tested for concentrates consisting of glucose×$H_2O$/sodium chloride, or $NaHCO_3$/sodium chloride under the same conditions.

The glucose×$H_2O$/sodium chloride concentrate container showed caking behaviour.

In the case of the $NaHCO_3$/sodium chloride concentrate, no significant water uptake was found.

These results show that the use of a barrier film reduces the water uptake, but does not completely prevent said uptake. By providing $NaHCO_3$/sodium chloride separately in a compartment without other components according to the invention, the water uptake and caking can be prevented.

EXAMPLE 3

The water uptake and the caking behaviour of a conventional dry concentrate was tested using two concentrate containers, with or without a gas barrier respectively, each comprising the following concentrate components:
Glucose with crystal water, $C_6H_{12}O_6 \times H_2O$
Magnesium chloride with crystal water, $MgCl_2 \times 6H_2O$
Calcium chloride with crystal water, $CaCl_2 \times 2H_2O$
Potassium chloride, KCl
Citric acid, $C_6H_8O_7$ The container comprised of film material without appreciable gas-barrier properties is depicted on the left of FIG. 1. Polypropylene, -PP-, polyethylene, -PE-, styrene ethylene butylene styrene block copolymer, -SEBS-, were used for producing said film. The container shown on the right of FIG. 1 comprised the same materials. Additionally, said film comprised a gas-barrier layer of silicon oxide. The gas permeability of said film was below 20 $cm^3/(m^2 \cdot d \cdot bar)$ for $CO_2$, as measured in accordance with DIN 53380—part 4. The containers were stored in a climate chamber at 40° C. and at a relative humidity of 75% for two weeks. In both cases, caking was observed; additionally, a brown discolouration was observed, which may indicate the degradation of glucose. Caking of the components in the two concentrate containers after 2 weeks under the conditions mentioned above is shown in FIG. 1.

EXAMPLE 4

Figure 3:
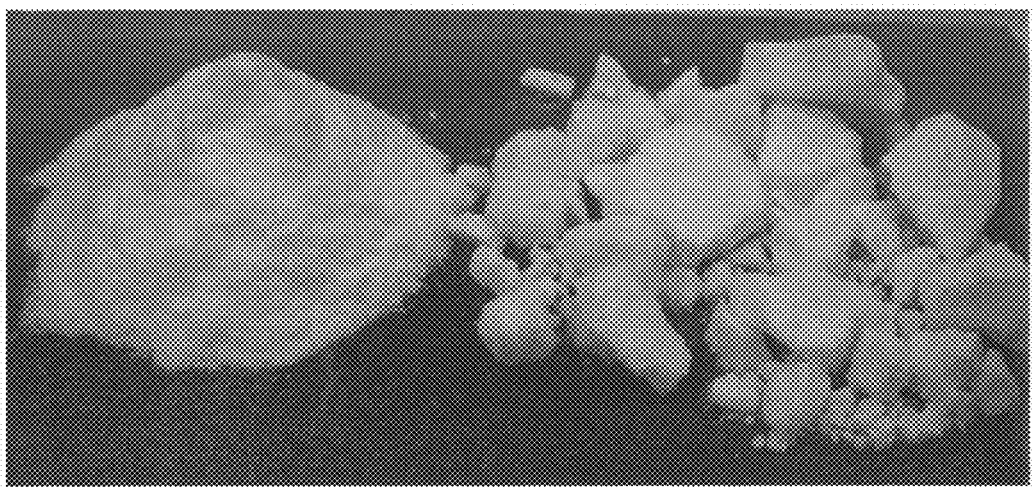
FIG. 3 is a photograph showing the caking of a conventional concentrate over a period of six months at 40° C. and 75% relative humidity, as discussed in Example 4.

The stability of a concentrate comprised of components according to the invention versus conventional components was tested. As shown in FIG. 3, caking occurred in a conventional concentrate which consisted of glucose×$H_2O$/sodium chloride and which was originally in powder form (left of FIG. 3, T=0 months) upon exposure of the concentrate container to 40° C. and 75% relative humidity in the climate chamber (depicted on the right of FIG. 3, T=6 months). It was assumed that the crystal water of the glucose in conjunction with sodium chloride caused caking. In addition, since sodium chloride exhibits a certain hygroscopy, the migration of water vapour through the film cannot be excluded.

In contrast, further experiments showed that anhydrous glucose according to the invention under the same test conditions does not promote caking, and is thus particularly useful for a multi-component dry concentrate composition.

EXAMPLE 5

Figure 4:
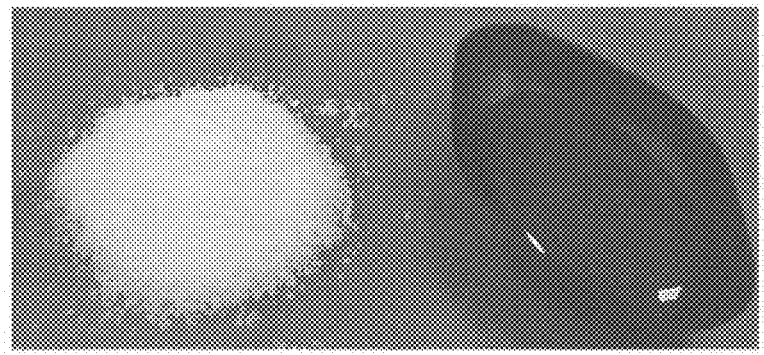
FIG. 4 is a photograph showing magnesium chloride liquefied by water uptake by exposure to 40° C. and 75% relative humidity in a gas-permeable concentrate container for a period of six month, as discussed in Example 5. The left panel shows the powdery $MgCl_2 \times 6H_2O$ components at time T=0 and the right panel shows the liquefied $MgCl_2 \times 6H_2O$ after 6 months exposure to the conditions above.

$MgCl_2 \times 6H_2O$ was stored in the climate chamber at 40° C. and 75% relative humidity in a gas-permeable concentrate container. The magnesium chloride liquefied by water uptake and by dissolving in its crystal water (see also FIG. 4: the left panel shows the initially powdery $MgCl_2 \times 6H_2O$ components at time T=0; the right panel shows liquefied $MgCl_2 \times 6H_2O$ after 6 months exposure to the conditions mentioned above).

EXAMPLE 6

Figure 5:
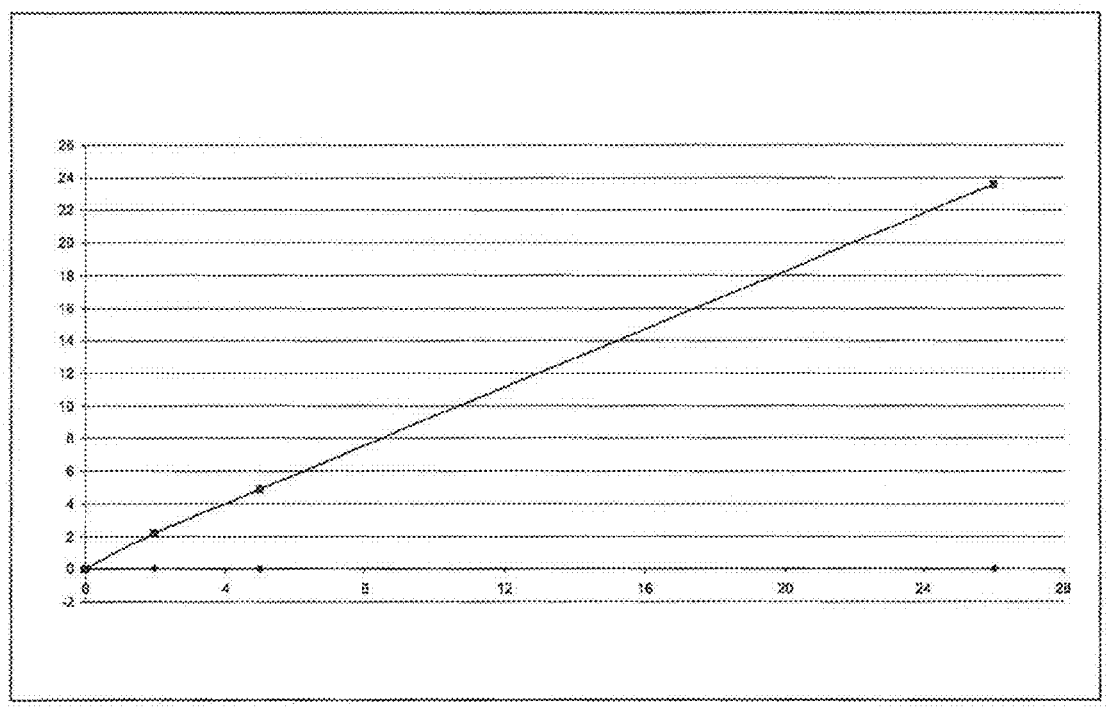
FIG. 5 is a graph illustrating water uptake into a concentrate container without a gas barrier of $MgCl_2 \times 6H_2O$ versus $4MgCO_3 \times Mg(OH)_2 \times 5H_2O$ over time, as discussed in Example 6.

The water uptake into a concentrate container without a gas barrier, comprising $MgCl_2 \times 6H_2O$ or alkaline magnesium carbonate, $4MgCO_3 \times Mg(OH)_2 \times 5H_2O$ respectively, was compared. The concentrate containers were each exposed in the climate chamber to 40° C. and 75% relative humidity for several weeks. The alkaline magnesium carbonate did not absorb any water over a period of 6 months, whereas significant water uptake was observed with magnesium chloride. See also FIG. 5: the plot shows the water uptake into the concentrate container without a gas barrier containing $MgCl_2 \times 6H_2O$ (■), and $4MgCO_3 \times Mg(OH)_2 \times 5H_2O$ (♦), respectively. The time in weeks is plotted on the abscissa. The water content in percent by weight is plotted on the ordinate. There was no water uptake into the container containing alkaline magnesium carbonate at 40° C. and 75% relative humidity, even after about 26 weeks, whereas, after the same period, the water uptake into the concentrate container containing $MgCl_2 \times 6H_2O$ was almost 24%.

The invention claimed is:

1. A concentrate for producing a medical solution, wherein the concentrate comprises at least three spatially separated parts, wherein the first part comprises magnesium carbonate, anhydrous calcium chloride, and a physiologically acceptable acid selected from the group consisting of citric acid, malic acid, fumaric acid, isocitric acid, succinic acid and oxalic acid, and is suitable for use as the medical solution upon addition of an aqueous medium.

2. The concentrate according to claim 1, wherein the concentrate further comprises at least one electrolyte component, at least one osmotic component and at least one buffer component.

3. The concentrate according to claim 1, wherein the magnesium carbonate is $4MgCO_3 \times Mg(OH)_2 \times 5H_2O$.

4. The concentrate according to claim 2, wherein the at least one electrolyte component comprises potassium chloride.

5. The concentrate according to claim 2, wherein the at least one osmotic component comprises glucose.

6. The concentrate according to claim 5, wherein glucose is provided as a separate part of the concentrate.

7. The concentrate according to claim 2, wherein the at least one buffer component comprises sodium bicarbonate.

8. The concentrate according to claim 7, wherein sodium bicarbonate is provided as a separate part of the concentrate.

9. The concentrate according to claim 1, wherein the second part comprises glucose.

10. The concentrate according to claim 9, wherein the third part comprises sodium bicarbonate.

11. The concentrate according to claim 5, wherein the glucose is anhydrous glucose.

12. The concentrate according to claim 8, wherein sodium chloride together with the sodium bicarbonate is present as a separate part of the concentrate.

13. The concentrate according to claim 1, wherein the physiologically acceptable acid is citric acid.

14. The concentrate according to claim 1, wherein the concentrate is present in dry form.

15. The concentrate according to claim 1, wherein the concentrate is substantially free of magnesium chloride.

16. A concentrate for producing a medical solution, wherein the concentrate comprises at least three spatially separated parts, wherein the first part comprises magnesium carbonate and/or anhydrous calcium chloride, the second part comprises glucose and the third part comprises sodium bicarbonate, and wherein the concentrate is suitable for use as the medical solution upon addition of an aqueous medium.

17. The concentrate according to claim 16, wherein the concentrate further comprises at least one electrolyte component.

18. The concentrate according to claim 16, wherein the magnesium carbonate is $4MgCO_3 \times Mg(OH)_2 \times 5H_2O$.

19. The concentrate according to claim 16, wherein the concentrate comprises anhydrous calcium chloride.

20. The concentrate according to claim 19, further comprising a physiologically acceptable acid selected from the group consisting of citric acid, malic acid, fumaric acid, isocitric acid, succinic acid and oxalic acid.

21. The concentrate according to claim 17, wherein the at least one electrolyte component comprises potassium chloride.

22. The concentrate according to claim 16, wherein the glucose is anhydrous glucose.

23. The concentrate according to claim 16, wherein the third part further comprises sodium chloride.

24. The concentrate according to claim 20, wherein the physiologically acceptable acid is citric acid.

25. The concentrate according to claim 16, wherein the concentrate is present in dry form.

26. The concentrate according to claim 16, wherein the concentrate is substantially free of magnesium chloride.

* * * * *